United States Patent [19]

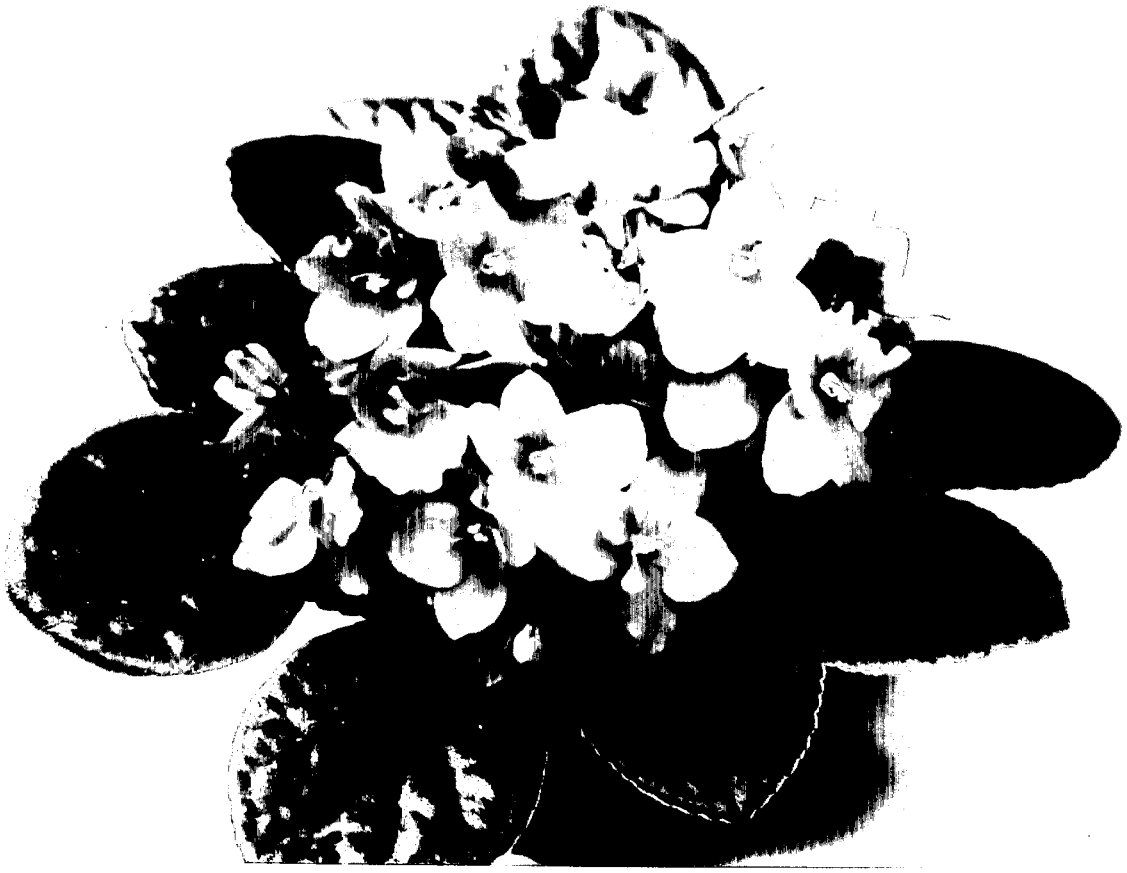

Holtkamp

[11] Patent Number: Plant 5,805

[45] Date of Patent: Nov. 18, 1986

[54] AFRICAN VIOLET PLANT NAMED IMPROVED NORTH CAROLINA

[75] Inventor: Reinhold Holtkamp, Isselburg, Fed. Rep. of Germany

[73] Assignee: Gessellschaftsvertrag uber die Ergindergemeinschaft "Optimara", Fed. Rep. of Germany

[21] Appl. No.: 568,440

[22] Filed: Jan. 5, 1984

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of African violet plant named Improved North Carolina characterized by its very strong and upright flower stems, each of which carries up to 15 flowers which are large and single in form and an intense red-purple in color, profuse flowering, vigorous growth habit, and by its attractive dark green leaves.

1 Drawing Figure

1

The present invention comprises a new and distinct cultivar of African violet plant, botanically known as *Saintpaulia ionantha,* and named Improved North Carolina.

The new cultivar was referred to during the breeding and selection process by the designation E 61/3, and is a product of a planned breeding program. The basic objective of the breeding program was to improve certain characteristics of the cultivar North Carolina, disclosed in my U.S. Plant Pat. No. 4,415.

The new cultivar was orginated from a cross made in a controlled breeding program in Isselburg, West Germany. The female, or seed parent was a cultivar designated B 15/12 red single. The male, or pollen parent was a cultivar designated 63 Red Frilled.

The new cultivar Improved North Carolina was discovered and selected by me as a flowering plant within the progeny of the stated cross in a controlled environment in Isselburg, West Germany. Asexual reproduction of the new cultivar by leaf cuttings and by division of shoots, as performed by me at Isselburg, West Germany, has demonstrated that the combination of characteristics as herein disclosed for the new cultivar are firmly fixed and are retained through successive generations of asexual reproduction.

Improved North Carolina has not been observed under all possible environmental conditions. The phenotype may vary signifiantly with variations in environment such as temperature, light intensity and day length. The following observations, measurements and values describe the new cultivar as grown in Isselburg, West Germany, and Nashville, Tenn. under greenhouse conditions which closely approximate those generally used in commercial practice.

The following traits have been repeatedly observed and are determined to be basic characteristics of Improved North Carolina, which in combination distinguish this African violet as a new and distinct cultivar:

1. Very strong and upright, wire-like stems, which normally number 9 or more.

2. An intensive red-purple flower color, with the flowers being relatively large in diameter and single form.

3. A profuse blooming habit, with 9–15 flowers being carried on each flower stem.

2

4. Excellent growth habit, producing a relatively large plant.

5. Attractive dark green, velvety leaves.

6. Continuous flowering, with the flowers being long lasting and non-dropping.

The new cultivar is most similar to, and was specifically intended to improve upon the characteristics of, my previously patented cultivar North Carolina. In comparison to North Carolina, the new cultivar is principally distinguished by its larger flowers, somewhat more oblong petals, a much greater abundance of very strong and upright flower stems, each of which carries 9–15 flowers, thereby making Improved North Carolina much more floriferous, and by its improved growth habit.

The accompanying photographic drawing shows a typical specimen plant of the new cultivar. The photograph shows the size, shape and abundance of the flowers, but is not accurate with regard to flower color. The flower color generally corresponds to the flower color of North Carolina, and is more purple than the flower color illustrated.

In the following description, color references for the leaves are made to The Royal Horticultural Society Colour Chart (R.H.S.), and flower color references are made to The Horticultural Color Chart (H.C.C.), except where general colors of ordinary significance are referred to. Color values were taken under natural light conditions at approximately 10 A.M. in late November in Nashville, Tenn. Under cooler finishing conditions, the flower color will be somewhat more intensive, and under relatively high finishing temperatures, the colors will fade somewhat.

Botanical classification: *Saintpaulia ionantha,* Ramat. cv Improved North Carolina.

Parentage:

*Male parent.*—63 Red Frilled.

*Female parent.*—B 15/12 red single.

Propagation: The new cultivar holds its distinguishing characteristics through successive propagations by leaf cuttings and by division of shoots.

Plant: From 9 cm. to 12 cm. tall when grown in pots, and approximately 22–28 cm. in diameter when fully grown.

*Leaves.*—General Form: Oval to heart shape. Diameter: 65–75 cm. Texture: Leather-like. Aspect: Velvety, hairy, slightly shiny. Veins: Well pronounced, light green to brownish green; very hairy. Color (upperside): Yellow green 147A. Color (underside): Brownish green. Petiole: Brownish green; very hairy; strong.

*Flowers.*—Buds: Ball shape. Sepals: 5, hairy. Color: Dark brown. Calyx: Funnel shape. Aspect: Spear shape; dark brown; hairy. Peduncle: Very short; strong; very hairy; upright.

*Individual flowers.*—Size: 45–50 mm. Color: Upperside: HCC 732. Underside: HCC 732/2.Borne: On strong upright flower stems. Shape: Violet shape. Corolla: Compact and full flower head above the leaves. Flowering time: In 9–10 weeks after potting, a mature plant with a full bouquet is formed.

*Reproductive organs.*—Anthers: 2 anthers composed of 4 cells. Filaments: Light green; hairy.

Styles: Red purple hairy glassy stigma. Pollen color: Yellow.

*Roots.*—White when young and active; brownish when older.

*Disease resistance.*—Good as experienced to date.

General observations: Improved North Carolina is a vigorous grower producing a relatively large plant with symmetrical dark green leaves. At least nine strong and upright flower stems are produced, each of which carries up to 15 large, single, intense red-purple flowers which are long lasting and non-dropping. The cultivar is highly floriferous.

I claim:

1. A new and distinct cultivar of African violet plant named Improved North Carolina, as illustrated and described, and particularly characterized by its very strong and upright flower stems, each of which carries up to 15 flowers which are large and single in form and an intense red-purple in color, profuse flowering, vigorous growth habit, and by its attractive dark green leaves.

* * * * *